(12) United States Patent
Port et al.

(10) Patent No.: US 6,436,636 B1
(45) Date of Patent: Aug. 20, 2002

(54) METHODS FOR IDENTIFYING PHARMACOLOGICALS FOR THE TREATMENT OF HEART FAILURE

(75) Inventors: J. David Port, Denver, CO (US); Gary Brewer, Winston-Salem, NC (US)

(73) Assignees: Wake Forest University, Winston-Salem, NC (US); University Technology Corporation, Boulder, CO (US)

( * ) Notice: Subject to any disclaimer, the term of this patent is extended or adjusted under 35 U.S.C. 154(b) by 0 days.

(21) Appl. No.: 09/050,344

(22) Filed: Mar. 3, 1998

Related U.S. Application Data

(63) Continuation of application No. 08/516,545, filed on Aug. 18, 1995, now Pat. No. 5,733,728.

(51) Int. Cl.[7] .......................... G01N 33/53; C12Q 1/68
(52) U.S. Cl. .......................... 435/6; 435/7.1; 435/7.94; 436/504; 436/501
(58) Field of Search .......................... 435/6, 7.1, 7.94; 436/504, 501; 514/2, 44; 424/184.1, 278.1, 520, 115, 195.1

(56) References Cited

U.S. PATENT DOCUMENTS 4,376,110 A * 3/1983 David et al. ................ 436/513
5,733,728 A * 3/1998 Port et al.

OTHER PUBLICATIONS

Zhang, W. et al Molecular and Cellular Biology 13 (12): 7652–7665, Dec. 1993.*
Seaver, S. Genetic Engineering News 14: 16, 21, Aug. 1994.*
Sharp, Z. S. et al. Biochim. Biophys. Acta 1048m(2–3): 306–309, 1990.*
Lahiri, D. K. et al. Nucleic Acids Research 14 (10): 4077–4094, 1986.*
Tay, N. et al. Journal of Virology 68: 6841–6848, 1992.*
Huang, L–Y. et al. J. Biol. Chem. 268 (34): 25769–25775, Dec. 1993.*
Akashi, M. et al. Blood 83 (11): 3182–3187, Jun. 1994.*
Liew, C.C. et al. Proc. Natl. Acad. Sci. USA 91: 10645–10649, Oct. 1994.*
Bristow, M. R. et al. J. Clin. Invest. 92: 2737–2745, Dec. 1993.*
Harlow, E. et al. (Eds.) Antibodies, A Laboratory Manual, Cold Spring Harbor Laboratory, Cold Spring Harbor, NY. pp. 72–77, 92–97, 128–135, 141–157, 1988.*
Stein, C. A. et al. Science 261: 1004–1012, Aug. 1993.*
Farrell, R. E. RNA Methodologies: A Laboratory Guide for Isolation and Characterization, Academic Press, San Diego, CA, pp. 160; 185–190, 1993.*

* cited by examiner

*Primary Examiner*—Phillip Gambel
(74) *Attorney, Agent, or Firm*—Dann, Dorfman, Herrell and Skillman

(57) ABSTRACT

Methods are disclosed for treating heart failure. Methods are disclosed for screening pharmacologicals that inhibit the down-regulatory activity of AUF1 or AUF1-related polypeptide for β-adrenergic activity. Methods are disclosed for treating a patient with a high level of the AUF1 or AUF1-related gene.

9 Claims, 6 Drawing Sheets

1432 (stop codon)

......(UAG)GGCCCGGCGCGGGCGCGGACUCCGGCACGGCUCCCAGGGAACGAGGAGAGAUCUGUGUUUACUUAAGACCGAUAGCAGGU
GAACUCGAAGCCCACAAUCCUGUCUGAAUCAUCCGAGGCAAAGAGAAAAGCCACGACCGUUGCACAAAAGGAAAGUUUGGAAGGAUG
GGAGAGUGGCUUGCUGAUGUUCCUGUUGUUUUCUUUCUUCUCUCUUUUUUUUUUUUUUUUUUUUU
UCUGUUUGUGGUCCGGCCUUCUUUUUGUGUGUGAUGCAUCUUUAGAUUUUUUCCCCACCAGGUGGUUUUGCACACUCUC
UGAGAGGACCGGAGUGGAAGAUGGGGUUGGGGUUAGGGGAAGCAUUAGGGAGGCAUUAAAUCGAUCAUCGUCCGAUCCAUCCCUU
CCCGGGAACAGGAACACACUACCGACCAGAAUGAGGAGAAUGACAGUUGUCAAGACAUAGUUGCUUUCCAGAGAAAUUUCAUU
UUAAUUCUAAGUAAUGACUGCUGUAAUUCUGGGAACCACAGUUCAAGAAAUGUUCAGAGAAAUGUUA
AGCUCUUCUUGGAACAAGCCCCCACCACUGCUUUCCUUGUGUAGGGCAAACCCGCCGCCCUGGGAGGCUGAGGCUGAUUU
CUACCUCACACUGUGCAUUUGCACAGCAGAGAAAGACUUGUUUAUAGACUUGUUUAUAUAGUGGAAGACC
AGGGCGCAGAGCCUCUCUGUGACAUGACAUCUGUCAAUGAAGACAGGACAUUAAAAGAGCAGAGAAACAGUUCAGAUUAC
UGCACAUGUGGAUAAAACAAAAAAGAUCAUAGCAGUCGACAGAUG

METHODS FOR IDENTIFYING PHARMACOLOGICALS FOR THE TREATMENT OF HEART FAILURE

This application is a continuation of U.S. application Ser. No. 08/516,545, filed Aug. 18, 1995, issued Mar. 31, 1998 as U.S. Pat. No. 5,733,728, the entire disclosure of which is incorporated by reference herein.

The U.S. Government has a paid-up license in this invention and the right in limited circumstances to require the patent owner to license others on reasonable terms as provided for by the terms of Grant No. HL51239 awarded by the National Institutes of Health.

FIELD OF THE INVENTION

The present invention relates to the detection and treatment of heart failure based on the down-regulatory activity of the AUF1 or an AUF1-related polypeptide toward human $\beta$-adrenergic receptors.

BACKGROUND OF THE INVENTION

The condition of heart failure is associated with heightened activity of the adrenergic nervous system (Bristow et al., Circulation 82:(Suppl.I) 12–25 (1990)), the severity of failure correlating with increases in circulating and cardiac concentrations of the catecholamine, norepinephrine (Cohn et al., N. Engl. J. Med. 311:819–823 (1984)). As a consequence of this increased "adrenergic drive" the cardiac $\beta$-adrenergic receptor ($\beta$-AR)/G-protein/adenylyl cyclase pathway can become markedly desensitized. One major component of the desensitization is selective down-regulation of the dominant adrenergic receptor subtype within the human myocardium, the $\beta_1$-AR (Bristow et al., Circulation 82:(Suppl.I) 12–25 (1990); Bristow et al., Circ. Res. 59:297–309 (1986); Brodde et al., J. Cardiovasc. Pharmacol. 8:1235–1242 (1986); Bristow et al., J. Clin. Invest. 89:803–815 (1992)). Recently, it has been demonstrated that the observed decrease in $\beta_1$-adrenergic receptors in failing human heart is closely associated with a corresponding down-regulation of $\beta_1$-AR mRNA (Bristow et al., J. Clin. Invest. 92:2737–2745 (1993); Ungerer et al., Circulation 87:454–463 (1993)).

Experiments performed using hamster DDT1-MF2 smooth muscle cells (Hadcock et al., J. Biol. Chem. 264:19928–19933 (1989)) suggest that down-regulation of the endogenously expressed $\beta_2$-AR mRNA does not appear to be caused by a decrease in the rate of transcription; rather, it appears that agonist exposure decreases the half-life of $\beta$-AR mRNA from approximately 12 to 5 h (Hadcock et al., J. Biol. Chem. 264:19928–19933 (1989)). This regulatory mechanism has been demonstrated previously to be important for numerous mRNAs encoding proto-oncogenes, lymphokines and cytokines. For these gene products regulation of mRNA stability has also been associated with the interaction of the mRNA with a family of cytosolic proteins (Mr 30,000–40,000) that often bind to A+U-rich elements (ARE) commonly within the 3' untranslated region (3'UTR) of the mRNA. This interaction induces mRNA degradation by mechanisms poorly understood. However, for some mRNAs including those containing AREs (Savant-Bhonsale and Cleveland, Genes Dev. 6:1927–1939 (1992); Winstall et al., Mol. Cell. Biol. 15:3796–3804 (1995)), the degradation of mRNA may be associated with the process of translation. The cytosolic A+U-rich mRNA binding proteins are in general considered to be distinct from other mRNA binding proteins such as the heterogeneous nuclear ribonucleoproteins (hnRNPs) (Dreyfuss, Annu. Rev. Cell Biol. 2:459–498 (1986); McCarthy and Kollmus, TIBS 20:191–197 (1995)), however, the role of hnRNP A1 and C proteins as cytoplasmic factors regulating mRNA stability is currently undergoing reassessment (Gorlach et al., EMBO J. 11:3289–3295 (1992); Hamilton et al., J. Biol. Chem. 268:8881–8887 (1993)).

From previous studies (Port et al., J. Biol. Chem. 267:24103–24108 (1992); Huang et al., J. Biol. Chem. 268:25769–25775 (1993); Tholanikunnel et al., J. Biol. Chem. 270:12787–12793 (1995)) using cytosolic extracts produced from DDT1-MF2 hamster smooth muscle cells, the properties of a $\beta$-AR mRNA-binding polypeptide ($\beta$-ARB), which binds to hamster $\beta_2$-adrenergic and human $\beta_1$-adrenergic receptor mRNAs, have undergone preliminary characterization. Binding of $\beta$-ARB to mRNA was determined to involve regions of the 3'UTR of the hamster $\beta_2$-AR mRNA containing an ARE (Port et al., J. Biol. Chem. 267:24103–24108 (1992); Huang et al., J. Biol. Chem. 268:25769–25775 (1993)). In addition, agonist stimulation of the $\beta$-AR pathway or protein kinase A (PK-A) activation by a cAMP analogue resulted in significant up-regulation (3–4 fold) of $\beta$-ARB as detected by UV-crosslinking. Conversely, treatment of DDT1-MF2 cells with dexamethasone, which up-regulates $\beta_2$-AR mRNA, down-regulated $\beta$-ARB by ~50%. Therefore, agents that regulate hamster $\beta_2$-AR mRNA stability and abundance appear to affect reciprocally the abundance of $\beta$-ARB. Among the family of G-protein coupled receptors, the mRNAs of the hamster $\beta_2$-AR, the human $\beta_1$- and $\beta_2$-AR, and the thrombin receptor have all been demonstrated to interact with $\beta$-ARB (Port et al., J. Biol. Chem. 267:24103–24108 (1992); Huang et al., J. Biol. Chem. 268:25769–25775 (1993); Tholanikunnel et al., J. Biol. Chem. 270:12787–12793 (1995)). To date, the identity of $\beta$-ARB has remained unresolved.

The cytoplasmic RNA-binding polypeptide, AUF1 (A+U-rich element RNA-binding/degradation Factor) (Zhang et al., Mol. Cell. Biol 13:7652–7665 (1993)), has recently been cloned and characterized. AUF1 binds to the 3'UTRs of several highly regulated mRNAs including c-myc, granulocyte/macrophage colony-stimulating factor (GM-CSF), and c-fos. Further, there is evidence of "cause and effect" between AUF1 and regulation of mRNA stability in that partially purified AUF1 can selectively accelerate the degradation of c-myc mRNA in an in vitro mRNA decay system (Brewer, Mol. Cell. Biol. 11:2460–2466 (1991)).

SUMMARY OF THE INVENTION

The present invention involves a method of detecting in a biological sample the amount of the AUF1 or an AUF1-related polypeptide for indicating heart failure. This involves generating an antibody to the products of the AUF1 or an AUF1-related polypeptide. Then contacting the antibody with the biological sample and detecting the amount of immune complex formation as an indication of the amount of the polypeptide in the biological sample. A higher amount of immune complex formulation, than found in a normal cell, indicates that heart failure is present. The higher than normal amount of the AUF1 or an AUF1-related polypeptide is a result of a high level of the AUF1 or an AUF1-related gene. This higher than normal amount of AUF1 or AUF1-related polypeptide is involved in the compensatory response to heart failure and/or involved in the worsening the condition of heart failure. This detection procedure would preferably involve contacting a biological sample from a human patient with an antibody (e.g., monoclonal antibody) which specifically reacts with the polypeptide. Then determining the amount of immune complex formation present in the biological sample. A higher amount of immune complex formation, than found in a normal cell, indicates that heart failure is present. The biological sample can be obtained from human ventricular myocardium, serum, and blood cells.

Another method for determining heart failure is the use of probes that bind to the RNA of the AUF1 or an AUF1-related gene. This involves hybridizing an RNA extracted from a biological sample of a human patient with a probe specific for the gene. Then determining the degree of hybridization to the mRNA as an indication of the amount of the gene in the biological sample. A higher degree of hybridization, than found in a normal cell, indicates that heart failure is present.

Another aspect of the invention involves a method for detecting a pharmacological that inhibits the down-regulatory activity of the AUF1 or an AUF1-related polypeptide for limiting the expression of β-adrenergic receptor genes by decreasing the binding affinity of the polypeptide for the β-adrenergic receptor gene. This involves mixing the polypeptide, a radiolabeled ARE-RNA of the β-adrenergic gene, and the pharmacological. The resulting mixture is filtered through a membrane such as nitrocellulose. Pharmacologicals that inhibits the down-regulatory activity of the polypeptide do so by decreasing the binding affinity of the polypeptide for the ARE-RNA. Since the polypeptide binds to the membrane, the radiolabeled ARE-RNA complexed with the polypeptide will adhere by means of the polypeptide. Any decreased binding affinity is reflected by the decreased counts per minute (cpm) retained on the membrane reflecting the decreased amount of bound radiolabeled ARE-RNA as a result of the presence of the pharmacological.

An additional aspect of the invention provides a composition containing a pharmacological in a pharmacologically acceptable carrier, suitable for treating a human having a high level of the AUF1 or an AUF1-related gene. These pharmacologicals can include small organic molecules, peptides, antisense RNA to AUF1 or AUF1-related mRNA, and a mini-peptide inhibitor/competitor to AUF1 or AUF1-related polypeptide.

BRIEF DESCRIPTION OF THE DRAWINGS

FIG. 1 represents a nucleotide sequence of the 3' untranslated region of the human $\beta_1$-AR (SEQ ID NO:1). The 3'UTR of the human $\beta_1$-AR was sequenced from the previously cloned cDNA (Frielle et al., *Proc. Natl. Acad. Sci. USA*. 84:7920–7924 (1987)) using the dideoxy method. The nucleotide sequence begins with the stop codon (UAG) at nucleotide 1432 and extends for an additional 932 nucleotides. A uniquely long U-rich region constituting an ARE as well as several other A+U-rich regions which are potential AREs are in bold and underlined including the putative mRNA destabilizing sequence, "UUAUUUAU". Four canonical poly (A) addition sequences are shown in bold, underlined, italics.

DETAILED DESCRIPTION OF THE INVENTION

Figure 2:
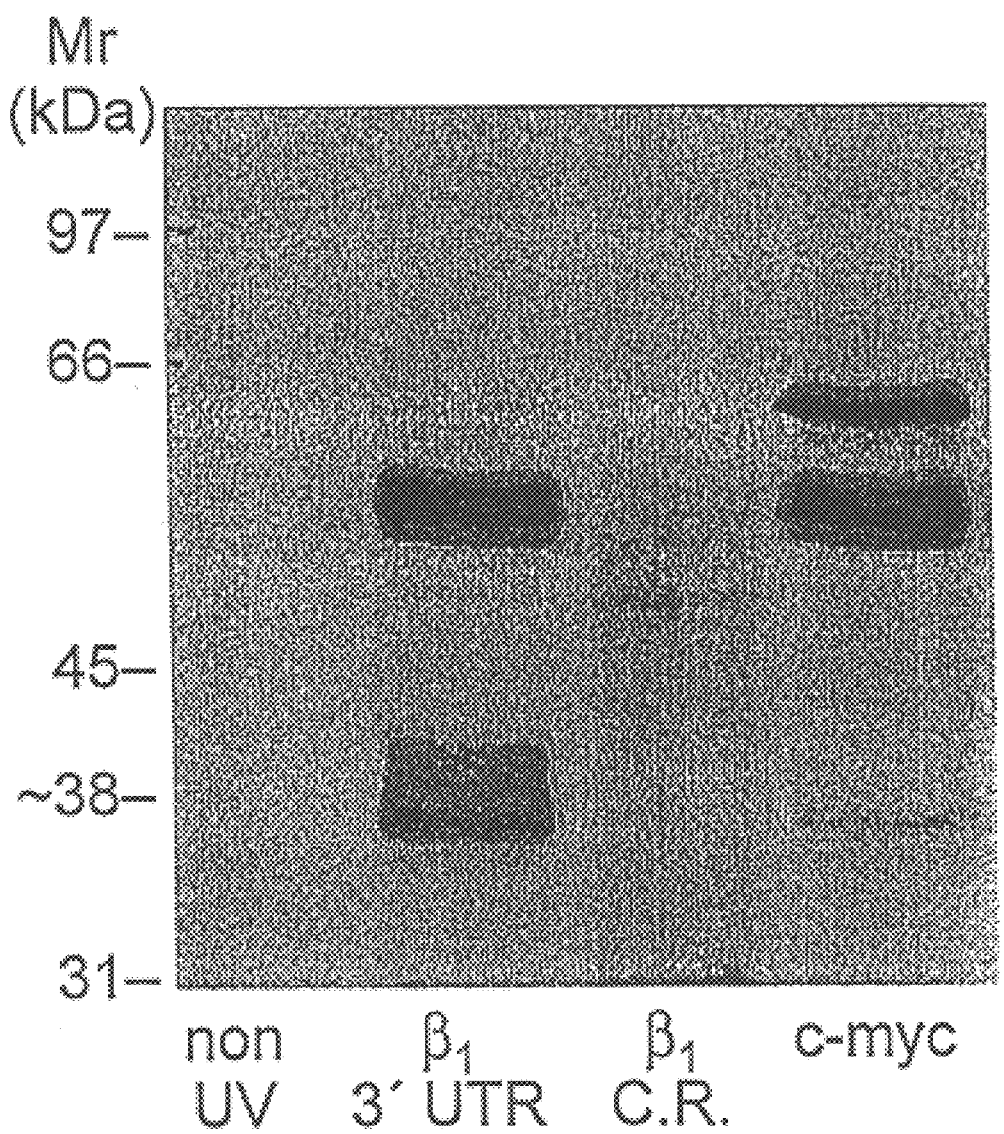
FIG. 2 represents an autoradiogram showing UV-crosslinking of ribosomal salt wash (RSW) proteins to multiple radiolabeled RNAs. Representative autoradiogram of RSW from DDT1-MF2 cells treated with (−)isoproterenol (10 $\mu$M for 48 h) and UV-crosslinked to capped, uniformly radiolabeled, in vitro transcribed RNAs. Equal amounts of RSW (20 $\mu$l, ~5×10$^5$ cell equivalents/$\mu$l) and equimolar amounts of radiolabeled RNA were added to each reaction. Lane 1, non UV-crosslinked control, Lane 2, $\beta_1$-AR 3'UTR only; lane 3, $\beta_1$-AR coding region (CR) only, lane 4, c-myc 3'UTR. A band of Mr 38,000, previously designated as β-ARB (Port et al., *J. Biol. Chem.* 267:24103–24108 (1992); Huang et al., *J. Biol. Chem.* 268:25769–25775 (1993); Tholanikunnel et al., *J. Biol. Chem.* 270:12787–12793 (1995)), is evident for the $\beta_1$-AR 3'UTR, and for c-myc but not for the $\beta_1$-AR CR only.

The present invention provides methods for detecting and treating heart failure which are based on the down-regulatory activity of the AUF1 or an AUF1-related polypeptide toward β-adrenergic receptors. The use of these polypeptides as described above is supported by the following associations: (1) human $\beta_1$-AR mRNA is down-regulated in the failing human heart, the physiological equivalent of agonist exposure; (2) $\beta_1$-AR mRNA stability is decreased by agonist exposure; (3) the 3'UTR of the human $\beta_1$-AR mRNA contains a consensus site for AUF1, and binds the AUF1 polypeptide, an mRNA binding polypeptide known to be involved in the rapid destabilization of c-myc mRNA; and (4) the AUF1 mRNA and polypeptide are up-regulated significantly by β-agonist exposure in DDT1-MF2 hamster smooth muscle cells and in the failing human heart (Blaxall et al., *FASEB J.* 9:A1277 (1995); Port et al., *FASEB J.* 9:A1277 (1995)).

The AUF1 polypeptide has several characteristics in common with the β-AR mRNA binding polypeptide, β-ARB, which shows they are the same or related polypeptides (Port et al., *J. Biol. Chem.* 267:24103–24108 (1992); Zhang et al., *Mol. Cell. Biol.* 13:7652–7665 (1993)). First, both polypeptides have similar electrophoretic mobilities. The apparent molecular weights of AUF1 are 37 and 40 kDa. Whereas, β-ARB was reported to be ~Mr 35,000 or 38,000. Second, both polypeptides are also present in the same cellular fractions. Third, β-ARB and AUF1 preferentially bind to the AREs of the same multiple mRNAs, such as 3'UTR of the human $\beta_1$-AR mRNA and GM-CSF. Finally, β-ARB can be immunoprecipitated from RSW using the anti-AUF1 antibody after the RSW has been crosslinked to the $\beta_1$-AR 3'UTR.

Expression of AUF1 in the Human Heart

In the failing human heart, $\beta_1$-AR mRNA and receptor protein are significantly down-regulated to a similar extent (Bristow et al., *J. Clin. Invest.* 92:2737–2745 (1993); Ungerer et al., *Circulation* 87:454–463 (1993)). Further, as discussed below, sequencing of the cDNA for the 3'UTR of the human $\beta_1$-AR has revealed that there is at least one potential ARE. Based on the precedent of agonist-mediated destabilization of the hamster $\beta_2$-AR mRNA ((Hadcock et al., *J. Biol. Chem.* 264:19928–19933 (1989)) and the binding of β-ARB to this mRNA (Port et al., *J. Biol. Chem.* 267:24103–24108 (1992)), it has been determined that the gene encoding the mRNA binding protein AUF1 was expressed in the human heart. Also it has been determined that AUF1 gene expression was affected by heart failure. Left ventricular myocardium was obtained from two groups (1) individuals with idiopathic dilated cardiomyopathy (IDC) (n=20) undergoing orthotopic cardiac transplantation, and (2) organ donors whose hearts were unsuitable for cardiac transplantation (n=14), but had normal contractile function (Nonfailing). To measure AUF1 and human $\beta_1$-AR mRNA, total cellular RNA was isolated from left ventricular myocardium. As determined by ribonuclease protection assay (RPA), the mRNA encoding AUF1 was significantly up-regulated in failing heart (190% of control, p<0.05, n=20) compared to nonfailing donor hearts (n=14). See Table 1.

TABLE 1

Expression of AUF1 mRNA and $\beta_1$-AR mRNA and protein in nonfailing and failing human left ventricular myocardium.

| Group | AUF1/18S mRNA ratio | $\beta_1$-AR mRNA by RT-PCR[#] | $\beta_1$-AR density (fmol/mg) |
|---|---|---|---|
| Nonfailing (n = 14) | 10 ± 2 | 3.8 ± 0.6 | 80 ± 8 |
| Failing (n = 20) | 19 ± 3* | 2.2 ± 0.3* | 31 ± 3* |

(X ± S.E.M.; *p < 0.05, unpaired t-test)
[#]10$^7$ molecules/µg poly(A) RNA

Relative AUF1 mRNA abundance was measured by RPA and referenced to the signal for 18S rRNA. The relative densitometric values or both AUF1 and 18S RNAs are arbitrary and dependent on the specific activity of each probe in each assay (a ratio of "2" does not imply twice as much AUF1 as 18S RNA). Absolute amounts $\beta_1$-adrenergic receptor mRNA were measured by quantitative RT-PCR from poly (A)-selected mRNA. β-AR density was measured in membrane preparations of human ventricular myocardium using multiple concentrations of the radioligand, $^{125}$ICYP to determine total adrenergic receptor binding. The density of the $\beta_1$-subtype was determined by competitive binding using the $\beta_1$-selective antagonist CGP20712A.

Heart failure had no effect on 18S rRNA expression. In several hearts, immunoblots were performed to insure that AUF1 protein was expressed. In each case, p37AUF1, p40AUF1, and p45 were detectable. The relative abundance of p37AUF was considerably less than that of either p40AUF1 or p45. Approximately 100 µg of total protein was necessary to detect p37AUF1 by immunoblot using ECL™ whereas p40 and p45 were readily detectable with 10 µg of total protein.

Consistent with previous findings (Bristow et al., *J. Clin. Invest.* 92:2737–2745 (1993)), $\beta_1$-AR mRNA abundance, as determined by quantitative RT-PCR, was significantly decreased (~40%) in failing as compared to nonfailing, control hearts (Table 1). β-AR density and subtype proportions also were determined in the same failing and nonfailing hearts. $\beta_1$-AR density was also significantly reduced (~61%) in failing compared to nonfailing hearts (Table 1). In summary, these data indicate that (1) AUF1 mRNA and protein are expressed in human ventricular myocardium; (2) in individuals with heart failure, AUF1 mRNA is significantly up-regulated; and (3) both $\beta_1$-AR mRNA and protein are down-regulated. From these data it is concluded that up-regulation of AUF1 in human heart is involved in the regulation of $\beta_1$-AR mRNA stability and thus is associated with the decline in $\beta_1$AR mRNA abundance in the failing heart.

Human $\beta_1$-AR 3'UTR

Although previously cloned (Frielle et al., *Proc. Natl. Acad. Sci. USA.* 84:7920–7924 (1987)), the nucleotide sequence of the 3'UTR of cDNA for the human $\beta_1$-AR had not been published. In order to determine if the $\beta_1$-AR 3'UTR contained potential mRNA stability regulatory domains such as an ARE and to facilitate mapping of mRNA-binding proteins, this portion of the cDNA was sequenced (FIG. 1). The $\beta_1$-AR 3'UTR contains a uniquely long poly (U) tract in its proximal region. This domain is similar to other AREs (Chen and Shyu, *Mol. Cell. Biol.* 14:8471–8482 (1994); Chen et al., *Mol. Cell. Biol.* 14:416–426 (1994)). Several other A+U-rich region are denoted including a putative mRNA destabilizing sequence "UUAUUUAU" (Lagnado et al., *Mol. Cell. Biol.* 14:7984–7995 (1994); Zubiaga et al., *Mol. Cell. Biol.* 15:2219–2230 (1995)). In addition, four potential poly (A) addition sites (AAUAAA or AUUAAA) are present. It is currently unknown which site or sites are used for poly (A) addition.

UV-Crosslinking of RSW and Recombinant p37AUF1 Polypeptide to the $\beta_1$-AR mRNA To determine which mRNA-binding proteins bind to the human $\beta_1$-AR mRNA, UV-crosslinking of radiolabeled RNA substrates to ribosome-associated proteins from isoproterenol (10 µM for 48 h) stimulated DDT1-MF2 cells was performed. Proteins were solubilized by a 0.3M KCl ribosomal salt wash (RSW). The rationale for using RSW rather than S100 cytosol or polysomes was that this preparation has been shown to contain AUF1 in a partially purified form as well as being sufficient to reproduce decay of proto-oncogene mRNA in an in vitro mRNA decay system (Brewer and Ross, *Mol. Cell. Biol.* 8:197–1708 (1988)). RNAs encoding the human $\beta_1$-AR coding region only, the $\beta_1$-AR 3'UTR only, or the c-myc 3'UTR, were in vitro transcribed and the radiolabeled RNAs incubated with RSW produced from isoproterenol treated DDT1-MF2 cells. Mixtures were UV irradiated, treated with Rnase A+T1 and separated by SDS-PAGE. A band at approximately Mr 38,000, previously designated as β-ARB (Port et al.,*J. Biol. Chem.* 267:24103–24108 (1992)), crosslinks to the 3'UTRs of the human $\beta_1$-AR and c-myc mRNAs but not to the coding region of the human $\beta_1$-AR mRNA (FIG. 2).

Figure 3A:
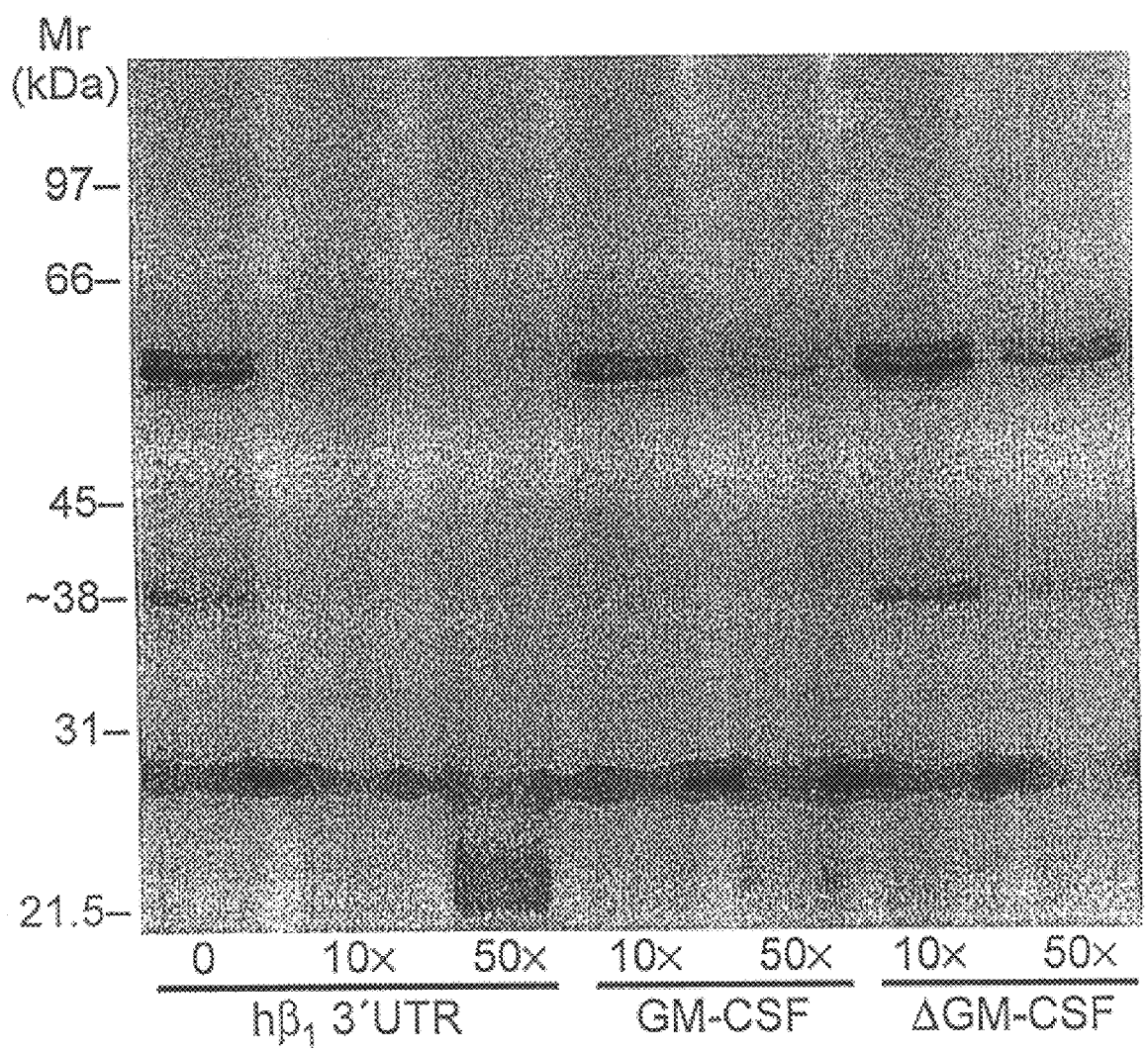
FIG. 3A represents an autoradiogram showing competitive displacement of β-ARB binding to $\beta_1$-AR 3'UTR RNA. Radiolabeled RNA corresponding to the 3'UTR of the human $\beta_1$-AR was UV-crosslinked to RSW proteins in the presence of increasing amounts (0-, 10-, 50-fold molar excess) of unlabeled competitor RNAs encoding the human $\beta_1$-AR 3'UTR (lanes 1–3), GM-CSF 3'UTR (lanes 4–5) and ΔGM-CSF (lanes 6–7). $\beta_1$-AR and GM-CSF, but not ΔGM-CSF competed effectively for β-ARB binding.
Figure 3B:
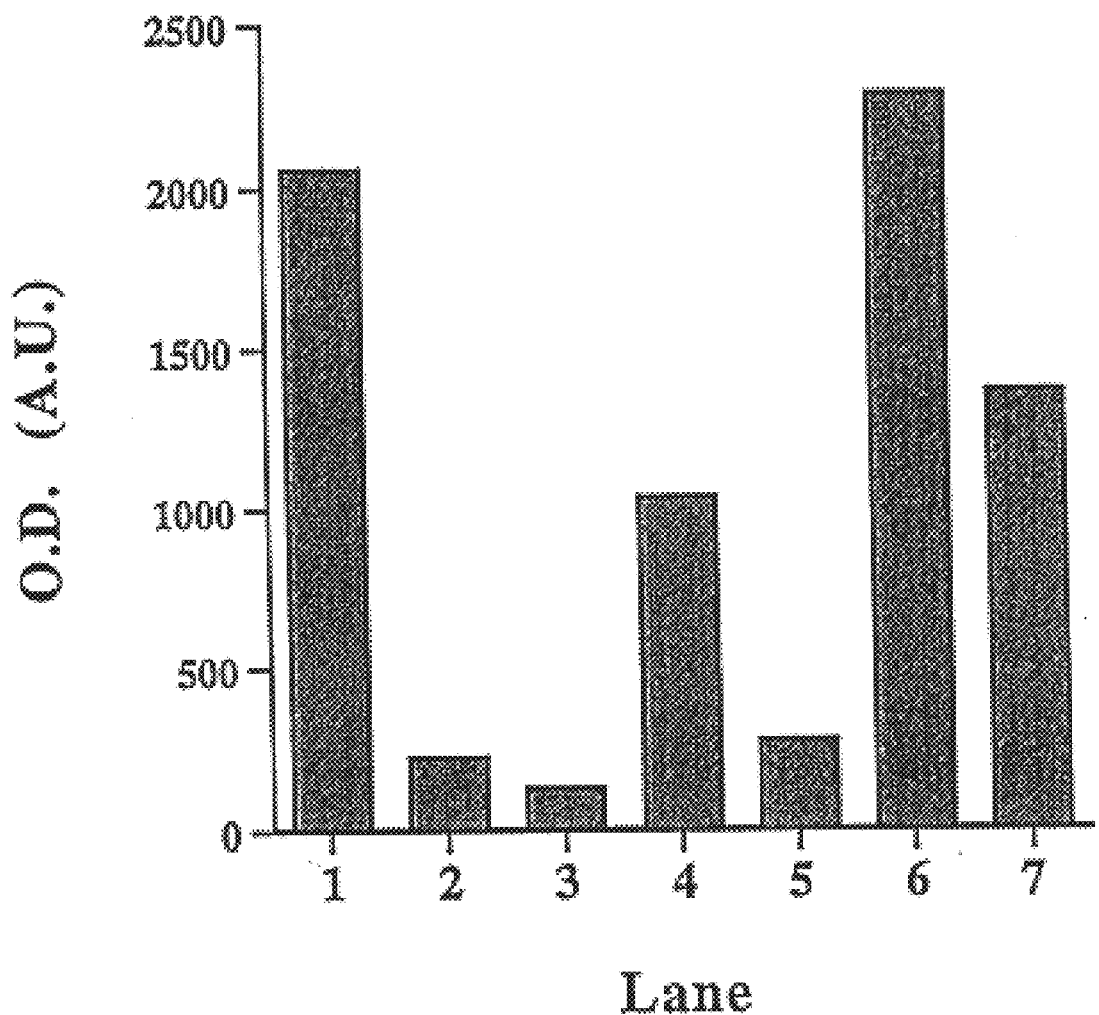
FIG. 3B is a bar graph showing the competition experiments depicted in FIG. 3A. The relative absorbance (O.D.) of the p38 band is expressed in arbitrary units (A.U.).

Binding of β-ARB to the $\beta_1$-AR 3'UTR is effectively competed by a 10-fold molar excess of unlabeled $\beta_1$-AR 3'UTR or by GM-CSF 3'UTR RNA but not by a 50-fold molar excess of ΔGM-CSF, an RNA that contains only one of the five pentameric AUUA motifs present in the wild-type RNA (FIGS. 3A & B). Unlabeled human $\beta_1$-AR 3'UTR RNA effectively and selectively competes for p38 binding at 10-fold molar excess. At 50-fold molar excess, unlabeled human $\beta_1$-AR 3'UTR displaces essentially all protein binding including an obvious doublet at ~Mr 55,000. In contrast, GM-CSF 3'UTR, even at 50-fold molar excess, effectively competes for β-ARB binding exclusively without affecting other protein binding. Therefore, although human $\beta_1$-AR 3'UTR and c-myc 3'UTR RNAs have similar protein binding profiles, only binding of β-ARB appears to be shared with similar affinities on the basis of competition assays.

Figure 4:
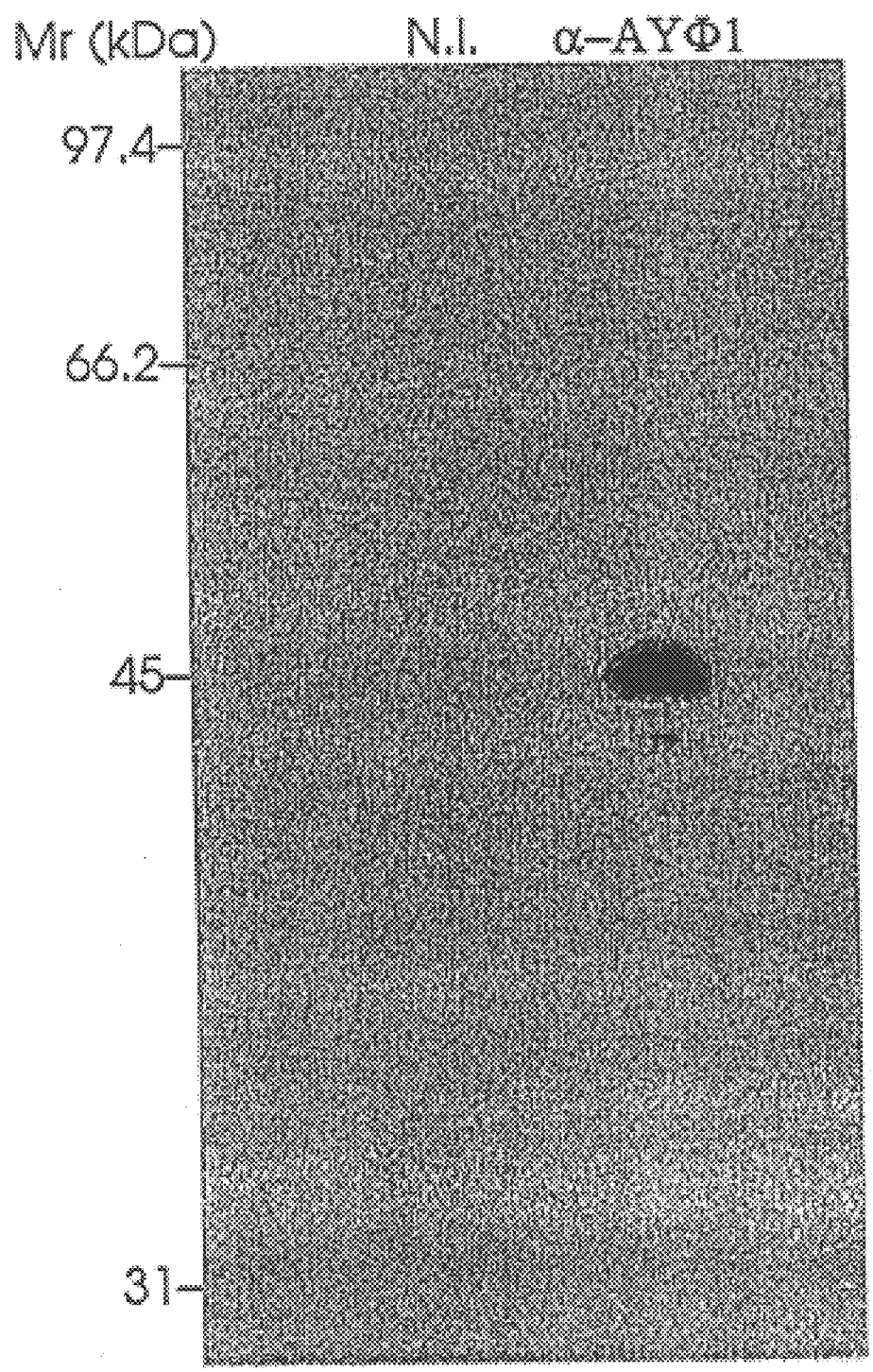
FIG. 4 represents an autoradiogram showing immunoprecipitation of AUF1 polypeptides from UV-crosslinking reaction. RSW proteins from DDT1-MF2 cells treated with isoproterenol (10 $\mu$M for 48 h) were pre-cleared with pre-immune serum. RSW (2×10$^6$ cell equivalents) was UV-crosslinked to 5×10$^6$ cpm of capped, uniformly labeled, in vitro transcribed RNA corresponding to the human $\beta_1$-AR 3'UTR. Following crosslinking, the reactions was treated with Rnase A+%1, diluted with NET-gel buffer (Zhang et al., *Mol. Cell. Biol.* 13:7652–7665 (1993)), and AUF1 polypeptides subjected to immunoprecipitation using polyclonal anti-AUF1 antiserum or non-immune serum. Proteins were resolved by SDS-PAGE and detected by autoradiography.

To show that β-ARB is AUF1 or an AUF1-related polypeptide, RSW proteins from isoproterenol (10 µM for 48 h) stimulated DDT1-MF2 cells were UV-crosslinked to radiolabeled $\beta_1$-AR 3' UTR, as described in Example 9. The reaction was immunoprecipitated with polyclonal anti-AUF1 or with non-immune serum. Compared to non-immune serum, anti-AUF1 serum selectively immunoprecipitated a single major protein with an Mr between ~37 to ~45 kDA (FIG. 4). A single band of weaker intensity is present just below the major band. This finding is in exact concordance with that of Zhang et al., *Mol. Cell. Biol.* 13:7652–7665 (1993) when immunoprecipitation AUF1 polypeptides UV-crosslinked to the c-myc ARE. No proteins were evident when immunoprecipitating with non-immune serum.

Figure 5:
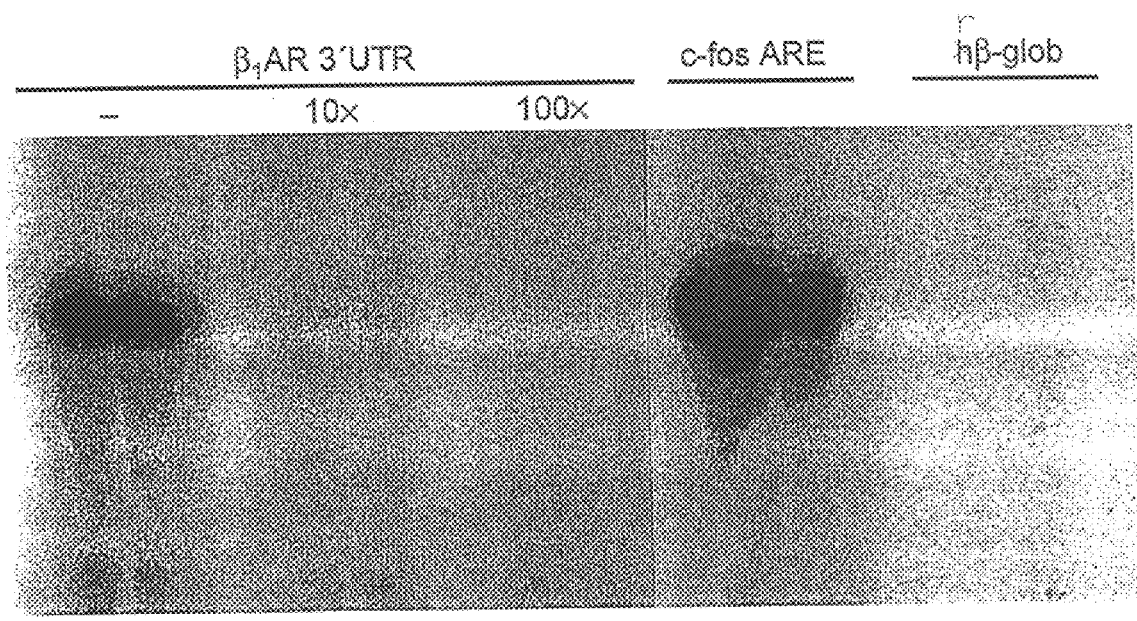
FIG. 5 represents an autoradiogram showing UV-crosslinking of purified, recombinant p37AUF1 polypeptide to human $\beta_1$-AR 3'UTR RNA. Autoradiogram of recombinant p37AUF1 UV-crosslinked to radiolabeled, in vitro transcribed human $\beta_1$-AR 3'UTR RNA. Lane 1, $\beta_1$-AR RNA in the absence of competitor RNA. Lanes 2 and 3, $\beta_1$-AR RNA is the presence of 10-fold and 100-fold molar excess of unlabeled β1-AR RNA. Lane 4, $\beta_1$-AR RNA in the presence of 100-fold molar excess of rabbit β-globin RNA (Rb). Lane 5, c-fos ARE only. Lane 6, rabbit β-globin RNA only.

To show AUF1 binds to the human $\beta_1$-AR 3'UTR, radiolabeled RNA was incubated with purified, recombinant p37AUF1, subjected to UV irradiation, Rnase A+T1 digestion, SDS-PAGE, and autoradiography. Recombinant p37AUF1 polypeptide binds to the $\beta_1$-AR 3'UTR and to the c-fos ARE but fails to bind to rabbit $\beta$-globin (R$\beta$) RNA (FIG. 5). Unlabeled $\beta_1$-AR 3'UTR RNA effectively competes for AUF1 binding, while a 100-fold molar excess of $\beta$-globin does not.

Together the crosslinking and immunoprecipitation experiments indicate that: (1) an Mr 38,000 polypeptide ($\beta$-ARB) from RSW UV-crosslinks to the 3'UTR but not the coding region of the human $\beta_1$-AR mRNA; a polypeptide of the same apparent molecular weight binds to c-myc and GM-CSF mRNA; (2) anti-AUF1 antibody immunoprecipitates Mr 38,000 $\beta$-ARB polypeptide crosslinked to the human $\beta_1$-AR 3'UTR; and (3) purified recombinant p37AUF1 binds to the 3'UTR of the human $\beta_1$-AR mRNA. These results show that Mr 38,000 $\beta$-ARB is AUF1 or an AUF1-related polypeptide.

Purification and isolation of the recombinantly expressed AUF1 or an AUF1-related polypeptide may be obtained by conventional means, e.g., preparative chromatographic separations and immunological separations involving monoclonal and/or polyclonal antibody preparations. This represents an opportunity to provide polypeptide for designing suitable diagnostic tests to detect the presence of heart failure in an organism.

For producing monoclonal antibodies, purified AUF1 or AUF1-related polypeptide is injected into mice at 3-week intervals for a total of 3 injections. After confirming antibody production by a test bleed, the spleen is removed. Spleen cells are fused to a mouse tumor cell line to immortalize the antibody producing cells. These antibody producing cell lines are cultured, and the culture supernatants are tested for reactivity to AUF1 or AUF1-related polypeptide by ELISA. Following identification of positive cell lines, the cells are cloned by limiting dilution to insure that the antibody is derived from only one cell type (i.e., is monoclonal). Each monoclonal antibody (MAb) is tested to determine the epitope recognized on the AUF1 or an AUF1-related polypeptide. Each is also tested to determine the assays that will permit the antibody to recognize AUF1 (e.g., Western blot, immunoprecipitation, indirect immunofluorescence in situ). The cell lines and their culture supernatants represent an unlimited supply of a particular MAb.

Increase of the AUF1 or an AUF1-related polypeptide levels or activity in cells leads to decreased $\beta$-adrenergic gene expression which is involved in the compensatory response to heart failure and/or involved in worsening the condition of heart failure. Thus, the AUF1 or AUF1-related MAbs are used as diagnostics to screen lysates of mononuclear cells from patients to assess the increase of the AUF1 or AUF1-related polypeptide. Screening of the lysates is performed by Western blotting and/or ELISA.

The anti-$\beta$-AR behavior of the AUF1 or an AUF1-related polypeptide is mediated by its affinity for an RNA sequence, known as an AU-rich element or ARE, present in the mRNA encoding the $\beta$-AR. The ARE targets these mRNAs for rapid degradation in normal cells. This degradation process serves to limit expression of the encoded proteins. Since the AUF1 or an AUF1-related cDNA is cloned into a bacterial expression vector, large amounts of the recombinant polypeptide can be easily purified. The recombinant polypeptide displays the same RNA-binding specificity and affinity as the cellular AUF1 or AUF1-related polypeptide. The ARE-binding affinity (i.e., dissociation constant, $k_D$) is easily measured by standard techniques (e.g., filter-binding assay, UV-crosslinking). Since the anti-$\beta$-AR properties of AUF1 or AUF1-related polypeptide are dependent upon its affinity for the ARE, screening of pharmacologicals that inhibit this activity is performed. This is done by mixing recombinant AUF1 or AUF1-related polypeptide, radiolabeled ARE-RNA, and the test-drug and filtering through a nitrocellulose membrane. The counts per minute (cpm) retained on the membrane is a function of the binding affinity of the polypeptide for the ARE. This is a rapid, convenient and quantitative assay to screen drugs that decrease the anti-$\beta$-AR capability of the polypeptide. The most effective drugs in this in vitro test are used to treat cells in culture to assess the drug's ability to inhibit the anti-$\beta$-AR activity of endogenous AUF1 or AUF1-related polypeptide. This is measured by increased growth rate and maturation of the $\beta$-AR in the cell.

Pharmacologicals are also tested to identify those that lower the affinity of AUF1 or AUF1-related polypeptide for the ARE in the assay described above. This results in elevated expression of genes involved in promoting $\beta$-AR growth. These drugs have utility in promoting proliferation of $\beta$-AR in cells.

The type of pharmacologicals that can be used to reduce the level of AUF1 or AUF1-related polypeptide in patients with heart failure include small organic molecules, peptides, antisense RNA to AUF1 or AUF1-related mRNA, and mini-peptide inhibitor/competitor to AUF1 or AUF1-related polypeptide. Both the antisense RNA and mini-peptide inhibitor/competitor can be expressed using gene therapy. In determining which antisense oligonucleotides are effective in reducing the level of AUF1 or AUF1-related polypeptide, the procedure is as follows. Deoxynucleotides complimentary to the 5' non-coding region and translation initiation codon of the AUF1 or AUF1-related mRNA are added to cultures of cells. The oligonucleotides enter the cells. This blocks translation of the AUF1 or AUF1-related mRNA and prevents synthesis of the polypeptide. Measuring the level of polypeptide in the cells gives an indication of the inhibiting effect of the antisense oligonucleotides.

The following examples are presented to illustrate the present invention and to assist one of ordinary skill in making and using the same. The examples are not intended in any way to otherwise limit the scope of the invention.

EXAMPLE 1

Tissue Procurement

Human ventricular myocardium was obtained from two categories of adult subjects. Failing hearts were obtained from patients undergoing heart transplantation for end stage heart failure (n=20) due exclusively to idiopathic dilated cardiomyopathy (IDC). These individuals had not received intravenous $\beta$-AR agonists, phosphodiesterase inhibitors, or $\beta$-blocking drugs prior to transplantation. Nonfailing hearts were obtained from adult organ donors whose hearts were unsuitable for cardiac transplantation due to blood type or size incompatibility (n=14). Organ donors' hearts had normal left ventricular function, as determined by echocardiography. Left ventricular aliquots were removed from the heart immediately upon explantation, and either immersed in liquid nitrogen for mRNA quantification or placed in ice-cold, oxygenated Tyrode's solution for preparation of material for radioligand binding assays, as described in Bristow et al., *Circ. Res.* 59:297–309 (1986).

EXAMPLE 2

Cell Culture

DDT1-MF2 cells were cultured in Dulbecco's modified Eagle's medium supplemented with 5% fetal bovine serum (Nyclone™, Logan Utah), penicillin (60 $\mu$g/ml) and streptomycin (100 $\mu$g/ml) as described in Port et al., *J. Biol. Chem.* 267:24103–24108 (1992). Cells were treated with either $\beta$-AR agonist 1$\mu$M (-)isoproterenol, or vehicle (1 mM ascorbic acid) as described in each individual Example.

EXAMPLE 3

AUF1 mRNA Measurement

A 233 base pair fragment of p37AUF1 cDNA (Zhang et al., *Mol. Cell. Biol.* 13:7652–7665 (1993)) was cloned from human heart DNA by the use of reverse transcription-polymerase chain reaction (RT-PCR). Primers utilized for this reaction spanned a segment of the human p37AUF1 coding region cDNA sequence from nt. 471 to nt. 702 (Zhang et al., *Mol. Cell. Biol.* 13:7652–7665 (1993)) and incorporated restriction enzyme recognition sites at the 5' ends (sMA I for the forward primer and Xba I for the reverse primer). Primer sequences were: 5'-CCCGGGAAGCTTGGGAAAATGTTATAGGAGGCC-3'(SEQ ID NO:2) for the forward primer, and 5'-GATCTCTAGAGCTTTGGCCCTTTTAGGATC-3'(SEQ ID NO:3) for the reverse primer. The PCR product was subcloned into pBluescript II KS (Stratagene, Inc., La Jolla, Calif.) and sequenced using the dideoxy method (Sequenase Ver. 2, USB, Cleveland, Ohio). Radiolabeled antisense riboprobes were transcribed from the Hind III digested p37AUF1 cDNA fragment using T7 DNA-dependent RNA polymerase, [$\alpha$-$^{32}$P]UTP (800 Ci/mmol, New England Nuclear, Boston, Mass.) and the Maxiscript™ kit (Ambion, Inc., Austin, Tex.). Total cellular RNA from human ventricular myocardium or from DDT1-MF2 cells was extracted by the method of Chomczynsky and Sacchi, *Anal. Biochem.* 1622:156–159 (1987) using RNA Stat-60 (Tel Test, Inc., Friendswood, Tex.), and quantified by absorbance at $A_{260}$. In each ribonuclease protection assay (RPA), 10 $\mu$g of RNA were hybridized overnight with $10^6$ cpm of radiolabeled AUF1 riboprobe and a low specific activity 18s rRNA riboprobe (Ambion, Inc.) using the RPA II kit (Ambion Inc.). Since 18S rRNA abundance is in excess of mRNAs, 18S probe was produced at a low specific activity to assure molar excess of probe to target without producing a signal beyond the linear range when measured simultaneously with AUF1. The hybridization reaction was digested with Rnase A and Rnase T1. RNA-RNA hybrids were resolved by electrophoresis in an 8%. polyacrylamide/8M urea gel. Protected fragments corresponding to AUF1 and 18S rRNA signals were quantified using a PhosphorImager (BioRad Laboratories, Hercules, Calif.).

EXAMPLE 4

$\beta_1$-AR mRNA Measurement

Human $\beta_1$AR mRNA abundance from human ventricular myocardium was measured by quantitative RT-PCR as described in Bristow et al., *J. Clin. Invest.* 92:2737–2745 (1993). Briefly, poly (A)$^+$-enriched RNA was extracted from samples of human ventricular myocardium using oligo(dT) cellulose (Micro-Fast Track™ mRNA Isolation Kit Ver. 1.2, Invitrogen Corp., San Diego, Calif.). mRNA was subjected to a reverse transcriptase reaction in the presence of a fixed amount of synthetic (84mer) RNA "internal standard" such that target mRNA ($\beta_1$AR) and "internal standard" were amplified colinearly. PCR primers were end-labeled with [$\gamma$-$^{32}$P]-ATP and the absolute amounts of $\beta_1$-AR and internal standard PCR products were determined for each heart by linear modeling of at least 3 points on the linear portion of the amplification curves.

EXAMPLE 5

$\beta_1$-AR Quantification $\beta_1$-AR density from human ventricular myocardium was determined in a crude membrane fraction as described in Bristow et al., *Circ. Res.* 59:297–309 (1986). Briefly, the total population of $\beta_1$ receptors was measured by the non-selective radioligand [$^{125}$I]iodocyanopindolol (ICYP) with and without the use of 1 $\mu$M 1-propranolol to determine total and nonspecific binding, respectively. Maximum binding (Bmax) and ICYP dissociation constant ($K_d$) were determined by nonlinear least-squares computer modeling of the specific binding curve. $\beta_1$-AR subtype proportion was determined using the $\beta_1$-AR selective ligand CGP-20712A (Bristow et al., *Circ. Res.* 59:297–309 (1986)). Protein concentrations were determined by the Peterson modification of the method of Lowry (Peterson, *Anal. Biochem.* 83:346–356 (1977)).

EXAMPLE 6

Sequencing of the cDNA Encoding the Human $\beta_1$-Adrenergic Receptor 3'UTR The ~2.4 kb cDNA encoding the human $\beta_1$-AR (Frielle et al., *Proc. Natl. Acad. Sci. USA.* 84:7920–7924 (1987)) was subcloned into pBluescript II KS at the Eco RI site and its orientation confirmed by DNA sequencing. Nucleotide sequence was determined from purified, double stranded plasmid DNA by the dideoxy method (Sequenace V2, USB). Sequencing primers corresponding to the published sequence of the $\beta_1$-AR coding region and to the T3 primer were used initially. Internal primers were used once additional sequence had been established. TAQ-uense DNA sequencing kit (USB) was used to sequence the T-rich portion of the cDNA. Each DNA strand was sequenced at least twice to insure accuracy. The cDNA sequence of the 3'UTR of the human $\beta_1$-AR has been submitted to Genbank (U29690).

EXAMPLE 7

In Vitro Transcription of RNA for UV-Crosslinking

A 919 bp cDNA fragment corresponding to the $\beta_1$AR 3' UTR was synthesized by PCR and subcloned into pcDNA3 (Invitrogen) utilizing the Xho I and Xba I restriction endonuclease sites. The resulting vector was linearized with Xba I, and in vitro transcription was performed as described in Port et al., *J. Biol. Chem.* 267:24103–24108 (1992). Briefly, radiolabeled RNA was synthesized using T7 DNA-directed RNA polymerase and [$\alpha$-$^{32}$P]UTP (800 Ci/mmol, New England Nuclear) to produce uniformly labeled, 5'-capped RNA. After transcription, Rnase-free Dnase I was added to the mixture to remove template DNA. The labeled transcript was extracted with phenol/chloroform, precipitated with ethanol, resuspended in Rnase-free water, and maintained at −80° C. until use.

EXAMPLE 8

Purification of Recombinant p37AUF1 Polypeptide

The coding region of p37AUF1 resides on a 910 bp BsmAI fragment spanning nucleotides 236 to 1146 of the cDNA (Zhang et al., *Mol. Cell. Biol.* 13:7652–7665 (1993)). This fragment was blunted and inserted into the SmaI site of the pGEM7Z(+) vector (Promega) to yield the pGEM7Z/ P37CR plasmid. To generate the corresponding $His_6$-AUF1 fusion peptide expression vector, an Asp718-HindIII fragment from pGEM/P37CR was inserted into Asp718-HindIII digested pTrcHisB (Incitrogen) resulting in pTrcHisB/ P37CR. The reading frame of the $His_6$-AUF1 fusion polypeptide was confirmed by both dideoxy sequencing and reactivity of the fusion polypeptide with polyclonal AUF1 antiserum.

An *E. coli* TOP10 (Invitrogen) clone containing pTrcHisB/P37CR was induced to express plasmid-encoded protein by culturing with 1 mM isopropyl-β-D-thiogalactopyranoside (IPTG, US Biochemical). $His_6$-AUF1 fusion polypeptide was purified using the Xpress System™ (Invitrogen) under native conditions as described by the manufacturer. Selected fractions were electrophoresed, and the protein profile assessed by Coomassie staining. Fractions 4–11 were pooled, and human α-lactalbumin (Sigma) was added to the final concentration of 100 µg/ml to aid in preserving the activity of the recombinant AUF1 polypeptide during storage at −80° C. The concentration of purified recombinant AUF1 was determined by comparison with known amounts of BSA using Coomassie stained SDS-polyacrylamide gels and immunoblot analysis using anti-AUF1 polyclonal antiserum.

EXAMPLE 9

UV-Crosslinking

A 0.3M KCl ribosomal salt wash (RSW) was produced from DDT1-MF2 cells using the method of Brewer and Ross, *Methods in Enzynology* 181:202–209 (1990). UV-crosslinking was performed as described in Port et al., *J. Biol. Chem.* 267:24103–24108 (1992) Briefly, an aliquot of radiolabeled RNA ($1-4\times10^6$ cpm) was added to a mixture containing 20 µl of RSW (~$5\times10^6$ cell equivalents/µl) from DDT1-MF2 cells, 5 µg of yeast tRNA, 4 mM dithiothreitol, 5 µg heparin, and 65 units of Rnasin™ in a total volume of 50 µl. After incubation for 10 min. at 22° C., samples were placed in a ice slurry and exposed to short-wave (254 mm) UV radiation for 2 min. in a Stratagene (La Jolla, Calif.) Model 1800 UV Stratalinker. The crosslinked RNA was digested with Rnase A (0.5 mg/ml) and Rnase T1 (10 units/ml) at 37° C. for 30 min. Samples were solubilized in 50 µl of Laemmli loading buffer for 10 min. at 70° C., and proteins were resolved by SDS-PAGE. Gels were stained with Coomassie R-Blue (Sigma) followed by destaining and drying, and subjected to autoradiography for 1–5 days.

EXAMPLE 10

Immunoprecipitation of AUF1

RSW from DDT1-MD2 cells and radiolabeled human $\beta_1$-AR 3'UTR RNA were prepared as described in Example 9. RSW (~$2\times10^6$ cell equivalents) was mixed with $5\times10^6$ cpm of $\beta_1$-AR 3'UTR RNA, UV-crosslinked, and digested with Rnase A and T1 as described in Example 9. RSW was pre-cleared with preimmune serum and protein A Sepharose (Pharmacia) and immunoprecipitated as described by Zhang et al., *Mol. Cell. Biol.* 13:7652–7665 (1993) with the exception that anti AUF1 antibody was pre-coupled to protein A Sepharose. The pellet was resuspended in Laemmli buffer, boiled 5 min., and proteins resolved by SDS-PAGE (10%). Gels were dried, and radiolabeled proteins were visualized by autoradiography.

EXAMPLE 11

Treatment of Patients having High Levels of the AUF1 or an AUF1-Related Gene Therapy can be given to those individuals determined to have high levels of the AUF1 or an AUF1-related gene, and who therefore are at risk of heart failure.

To treat heart failure in these individuals, the pharmacological is administered therapeutically in an amount sufficient to inhibit down-regulation of the β-adrenergic receptor by the AUF1 or an AUF1-related polypeptide. An AUF1 or anti-AUF-related polypeptide dosage of the pharmacological is 1 to 500 µg/kilogram of body weight/day. The pharmacological can be administered by injection with a pharmacologically acceptable carrier, either alone or in combination with another agent. Acceptable pharmacological carriers are those which dissolve the pharmacological or hold it in suspension, and which are not toxic to the extent of permanently harming the patient. Preferred are aqueous solutions of salts or non-ionic compounds such as sodium chloride or glucose, more preferably at an isotonic concentration. Other agents may be present provided that they do not interfere with the action of the pharmacological. Those skilled in the art will know, or will be able to ascertain with no more than routine experimentation, particular pharmacological carriers for this composition.

As will be apparent to those skilled in the art in which the invention is addressed, the present invention may be embodied in forms other than those specifically disclosed above without departing from the spirit or essential characteristics of the invention. The particular embodiments of the present invention described above, are, therefore, to be considered in all respects as illustrative and not restrictive. The scope of the present invention is as set forth in the appended claims rather than being limited to the examples contained in the foregoing description.

---

What is claimed is:

1. A method of screening a pharmacological agent suitable for treatment of heart failure caused by down-regulatory activity of an AUF1 polypeptide binding a β adrenergic receptor mRNA, the method comprising;
   a) mixing the AUF1 polypeptide with a detectably labeled A+U-rich RNA element of the β-adrenergic receptor mRNA (ARE-RNA), in the presence or absence of a pharmacological agent suspected of lowering the binding affinity of AUF1 for said ARE-RNA;
   b) measuring, in the presence, as compared to the absence, of the pharmacological agent, the amount of detectably labeled ARE-RNA complexed with said AUF1 polypeptide, pharmacological agents which decrease said binding affinity of said AUF1 for said ARE-RNA and thereby decrease the anti-β-AR activity of said polypeptide being suitable for the treatment of heart failure.

2. A method as claimed in claim 1, wherein said A+U-rich RNA element is detectably labeled with a radiolabel.

3. A method as claimed in claim 1, wherein said binding affinity is measured in a filter binding assay performed in the presence or absence of said pharmacological.

4. A method as claimed in claim 1, wherein said binding affinity is measured by UV-crosslinking of said ARE-AUF1 polypeptide in the presence or absence of said pharmacological.

5. A method of screening a pharmacological that lowers binding affinity of an AUF1 polypeptide to an A+U-rich element (ARE) of β-adrenergic RNA, the method comprising:
   a) mixing the AUF-1 polypeptide with a detectably labeled A+U-rich element of β-adrenergic RNA in the presence or absence of said pharmacological suspected of lowering the binding affinity of AUF-1 polypeptide for said A+U-rich element of RNA;

b) measuring the amount of detectably labeled ARE-RNA complexed with said AUF1 polypeptide the presence, as compared to the absence, of the pharmacogical; thereby identifying pharmacologicals with said AUF1 polypeptide by lowering the binding affinity of said AUF1 for said ARE-RNA.

6. The method of claim 5 wherein the A+U-rich element naturally occurs in the β-adrenergic receptor mRNA.

7. A method as claimed in claim 5, wherein said A+U-rich RNA element is detectably labeled with a radiolabel.

8. A method as claimed in claim 5, wherein said binding affinity is measured in a filter binding assay performed in the presence or absence of said pharmacological.

9. A method as claimed in claim 5, wherein said binding affinity is measured by UV-crosslinking of said ARE-AUF1 polypeptide in the presence or absence of said pharmacological.

* * * * *

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
        (A) LENGTH: 668 base pairs
        (B) TYPE: nucleic acid
        (C) STRANDEDNESS: single
        (D) TOPOLOGY: linear (ii) MOLECULE TYPE: DNA (genomic)

-continued (xi) SEQUENCE DESCRIPTION: SEQ ID NO:1:

| | | | | | |
|---|---|---|---|---|---|
| AGGGCCCGGC | GCGGGGCGCG | GACCCGGGCA | CGGCCCCAGG | GGAACGAGGA | GACGGACAAG | 60
| ACCGAAGCAG | GGAACCGAAG | CCCACAACCC | GCGAACACCG | AGGCAAAGAG | AAAAGCCACG | 120
| GACCGGCACA | AAAAGGAAAG | GGGAAGGGAG | GGAGAGGGCG | CGAGCCGGCC | CCCCCGGGGC | 180
| CGGCCCGGGG | CGGGAGCACA | GACCCCCACC | AGGGGGCACA | CCCGAGAGGA | CCGGAGGGAA | 240
| GAGGGGGGAG | GGGAAGGGAG | AAGCAAGGGA | GGCAAAAACG | ACACGCCGAC | CCACCCCCCG | 300
| GGAACAGGAA | CACACACCGA | CCAGAGAGAG | GAGAAGACAG | GCAAGACAAC | CGCCCAGAGA | 360
| AACAAACAAG | AAGACGCGAG | AAAGCAAAGA | GAAAGGAGGA | GGCAAAAAAA | AAAAAACACG | 420
| CAAGAAAGAA | GCCCGGAACA | AGCCCCACCG | CCCGGAGGGC | AAACCCGCGC | CCCCGCGCGC | 480
| CGGGGGCAGG | CGAGGGACAC | CCACACGGCA | GCACAGCAGA | AGAAAGACGA | AAAACAGCAA | 540
| GACAAAAGGG | AAGGACCAGG | CGCAGAGCCC | CCGGACAGGA | CCGCAAGAAG | ACAGGACAAA | 600
| AAGAGAGCAG | AGAGAGAGAA | ACAGCAGAAC | GCACAGGGAA | AAAACAAAAA | AGACAAGCAG | 660
| CGACAGAG | | | | | | 668

(2) INFORMATION FOR SEQ ID NO:2:

(i) SEQUENCE CHARACTERISTICS:
      (A) LENGTH: 33 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:2:

CCCGGGAAGC TTGGGAAAAT GTTATAGGAG GCC                                   33

(2) INFORMATION FOR SEQ ID NO:3:

(i) SEQUENCE CHARACTERISTICS:
      (A) LENGTH: 30 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:3:

GATCTCTAGA GCTTTGGCCC TTTTAGGATC                                       30